(12) United States Patent
Jones et al.

(10) Patent No.: US 6,646,125 B1
(45) Date of Patent: Nov. 11, 2003

(54) PROCESS FOR THE SYNTHESIS OF CHLOROPURINE INTERMEDIATES

(75) Inventors: Martin Francis Jones, Stevenage (GB); Christopher John Wallis, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/529,385

(22) PCT Filed: Oct. 14, 1998

(86) PCT No.: PCT/GB98/03080

§ 371 (c)(1), (2), (4) Date: Apr. 25, 2000

(87) PCT Pub. No.: WO99/19327

PCT Pub. Date: Apr. 22, 1999

(30) Foreign Application Priority Data

Oct. 14, 1997 (GB) .............................................. 9721780

(51) Int. Cl.⁷ ...................... C07D 473/40; C07D 239/50
(52) U.S. Cl. ........................................ 544/277; 544/323
(58) Field of Search ......................................... 544/277

(56) References Cited

U.S. PATENT DOCUMENTS

| 4,268,672 A | * | 5/1981 | Vince .......................... 544/277 |
| 5,329,008 A | | 7/1994 | Partridge et al. |
| 5,763,607 A | | 6/1998 | Vince et al. |
| 6,156,893 A | * | 12/2000 | Bernegger .................. 544/277 |

FOREIGN PATENT DOCUMENTS

| EP | 0 434 450 A | 6/1991 |
| GB | 2 217 320 A | 10/1989 |
| WO | 91 15490 | 10/1991 |
| WO | 95 21161 A | 8/1995 |

* cited by examiner

*Primary Examiner*—Mark L Berch
(74) *Attorney, Agent, or Firm*—Amy H. Fix

(57) ABSTRACT

The present invention relates to a process for the preparation of a carbocyclic purine nucleoside analogue of formula (I), its salts and pharmaceutically acceptable derivatives thereof which comprises hydrolysing a compound of formula (IV) wherein P is a protecting group, in the presence of an acid, condensing the product of formula (V) formed in situ in the presence of a base with a compound of formula (VI) followed by in situ ring closure of the resulting intermediate.

13 Claims, No Drawings

PROCESS FOR THE SYNTHESIS OF CHLOROPURINE INTERMEDIATES

The present invention relates to a process for the preparation of a carbocyclic purine nucleoside analogue of formula (I), its salts and pharmaceutically acceptable derivatives thereof. An enantiomerically pure compound of formula (I)

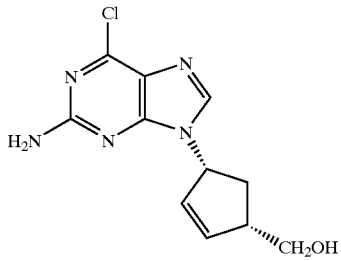

(I)

has been described in GB-A-2217320 and can be used as an intermediate in the manufacture of abacavir, a 2-aminopurine nucleoside analogue with the following structure (II)

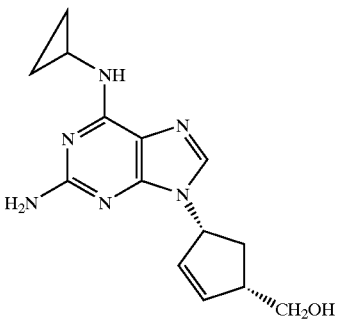

(II)

This is described in EP 0434450 as having potent activity against human immunodeficiency virus (HIV) and hepatitis B virus (HBV).

There exists a need to synthesise large quantities of abacavir for clinical trials and once abacavir has been approved by the national medicine regulatory agencies, large quantities of abacavir will also be required for sale as a prescription medicine for the treatment of HIV infections.

Processes for the manufacture of abacavir using enantiomerically pure compounds of formula (III)

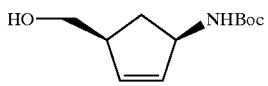

(III)

via the 2-aminopurine intermediate of formula (I) are described generally in PCT Publication Nos. WO91/15490, in WO95/21161, in EP 0434450 and in Tetrahedron: Asymmetry Vol. 4, p.1117, (1993). However, the procedures described provide an unsatisfactory route to the 2-aminopurine derivative of formula (I), inasmuch as they require the isolation and purification of a number of intermediates resulting in a relatively high cost and a low yield for the synthesis.

We have developed a process for the production of the intermediate of formula (I) from N-protected-4-aminocyclopentenes of formula (IV)

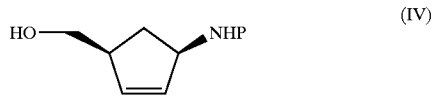

(IV)

wherein P is a protecting group, which provides a high yield and is more cost effective. The protecting group P will desirably be an acyl or substituted oxycarbonyl group.

One aspect of the present invention comprises an in situ conversion of cyclopentenes of formula (IV) to 2-aminopurine derivatives of formula (I) easily and conveniently without the need to isolate any intermediates. In our procedure, the deprotection of the starting material of formula (IV) in situ provides the desired amino alcohol without any wasteful workup, and because of the direct coupling and cyclisation, again without any work up or isolation of intermediates, the overall yield of the process is increased.

According to a further aspect of the invention, therefore, we provide a process for the preparation of a compound of formula (I),

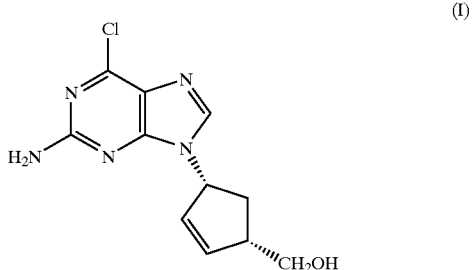

(I)

optionally in the form of its salt or complex, which comprises hydrolysing a compound of formula (IV) as defined above in the presence of acid, condensing the product of formula (V) formed

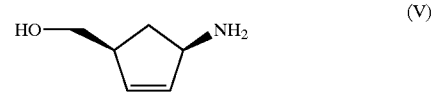

(V)

in situ in the presence of a base with a compound of formula (VI)

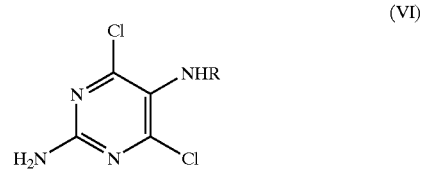

(VI)

in which R represents CHO or H, followed by ring closure in situ of the resulting intermediate of formula (VII)

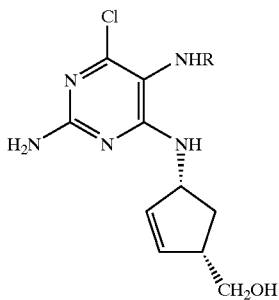

(VII)

in which R represents CHO or H, to produce a compound of formula (I), which can then be optionally reacted with an acid or complexing agent to form its salt or complex.

As described above, preferred protecting groups in the compound of formula (IV) are acyl or substituted oxycarbonyl groups. Preferred acyl groups include formyl or lower alkanoyl (having e.g. 1 to 4 carbon atoms in the alkyl portion), especially an acetyl group. Preferred substituted oxycarbonyl groups will be of the formula R' OC(O)—, wherein R' may be an alkyl or aralkyl group. A preferred! alkyl group is tert butyl; a preferred aralkyl group is benzyl.

The hydrolysis step is preferably achieved by mild acid-catalysed hydrolysis in an organic solvent, such as an alkanol, a cyclic ether or a chlorinated hydrocarbon. It is preferred to use an organic or mineral acid such as trifluoroacetic acid or hydrochloric acid in an alkanol solvent such as industrial methylated spirit (IMS), optionally in the presence of water.

The condensation step is then carried out without any isolation of the hydrolysis product of formula (V) This condensation reaction is preferably carried out under reflux in a polar solvent such as an alcohol, e.g. ethanol or butanol, or water or acetonitrile, or mixtures thereof, in the presence of at least sufficient base to neutralise both the acid used for the hydrolysis and that produced during the condensation. Generally, there will be at least 2 equivalents based on the amount of compound of formula (IV). The base will desirably be a trialkylamine or an alkali metal carbonate or bicarbonate, e.g. potassium or sodium carbonate, and more preferably, sodium bicarbonate. Preferred combinations are triethylamine or sodium bicarbonate in IMS. The group R in the compound of formula (VI) preferably represents CHO.

The ring closure reaction is then carried out, again without any isolation of any preceding intermediate product of formula (VII). This is conveniently carried out using trialkylorthoformates in the presence of concentrated aqueous or anhydrous mineral acid, optionally in the presence of one or more non-aqueous solvents, e.g. tetrahydrofuran, ethyl acetate or IMS. Suitably, the unisolated product of formula (VII) is added to a mixture of acid and a trialkylorthoformate. A preferred combination comprises use of from about 1.5 to 3, preferably around 2 molar equivalents of hydrochloric acid in triethylorthoformate, which results in precipitation of the hydrochloride salt of the 9-substituted-2-amino purine of formula (I). The free base may, if desired, be liberated by treatment with base.

The process of the invention has been found to provide yields of compounds of formula (I) starting from a compound of formula. (IV) of in excess of 80%. This compares very favourably with yields of compounds of formula (I) which are obtained using earlier stepwise procedures in which the intermediates are isolated, which give, typically around 56% when the compound of formula (III) is used as starting material, or yields of around 75% when the procedure described in Publication No. WO95/21161 is used, starting from a compound of formula (V).

The compounds of formula (VI) can be synthesised by a method as described in WO95/21161. The compound can be synthesised from the readily available 2,5-diamino-4,6-dihydroxypyrimidine, by reacting this with a Vilsmeier reagent of formula (VIII)

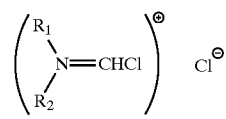

(VIII)

to form a compound of formula (IX)

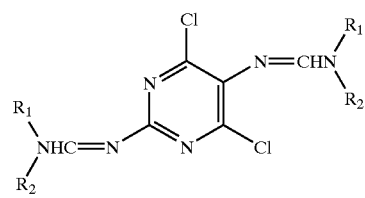

(IX)

(wherein in both formulae (VIII) and (IX), $R_1$ and $R_2$ are as defined in WO95/2:1161, viz: that $R_1$ and $R_2$, which may be the same or different are selected from $C_{1-8}$ straight-chain alkyl, $C_{1-8}$ branched alkyl, $C_{3-8}$ cycloalkyl, and aryl groups (such as phenyl or naphthyl), which may be optionally substituted, for example by $C_{1-4}$ alkyl or halogen (e.g. Cl). In a preferred embodiment of the invention $R_1$ and $R_2$ are both methyl), followed by hydrolysis.

Compounds of formula (VIII) may be prepared from a variety of formamides of secondary amines by reaction with a variety of acid halides, such as phosphorus oxychloride, phosphorus pentachloride, thionyl chloride, phosgene, and oxalyl chloride, for example as detailed in a review by C. M. Marson, Tetrahedon 1992, 48:3660–3720 and references therein.

The compound of formula (VI) where R is H can be prepared from the compound of formula (IX) by hydrolysis in acidic solution, e.g. at pH 3±0.5, by adding a water miscible cosolvent, such as ethanol. The compound of formula (VI) where R is CHO can also be prepared by the hydrolysis of the compound of formula (IX) in the minimum of water, with the pH controlled as described above. Under these conditions the compound of formula (VI) where R is CHO precipitates as formed and can be filtered off.

The compound of formula (IV) may be prepared by methods analogous to those described in Tetrahedron: Asymmetry Vol.4, p.1117 (1993).

The following Examples are intended for illustration only and are not intended to limit the scope of the invention in any way.

Example A

Preparation of (1S,4R)-cis-4-[2-amino-6-chloro-9H-purin-9-yl]-2-cyclopentene-1-methanol hydrochloride salt.

A suspension of (1R,4S)-cis-[4-(hydroxymethyl)-2-cyclopentene-1-yl]carbamic acid, 1, 1-dimethylethyl ester (100 g) in industrial methylated spirit (IMS) (600 ml) was treated with concentrated hydrochloric acid (48 ml, 1.2 molar equivalents) and the resultant solution was heated to the boil over about 0.5 h. Heating under reflux was maintained for about 2.5 h. The solution was cooled to 20 to 25° C. and diluted with IMS (600 ml). Triethylamine (170 ml) was added followed by N-(2-amino-4,6-dichloro-5-pyrimidinyl)formamide (WO95/21161) (97 g). The suspension was heated under reflux for about 17 h to give a clear solution, which was cooled to 25 to 30° C. and finely divided potassium carbonate (169 g) was added. The suspension was stirred in this temperature range for about 0.5 h then cooled to 0 to 5° C. and the solids filtered off. The solids were washed with IMS (3×180 ml and 1×140 ml) and the combined filtrates and washings were concentrated under reduced pressure to a red gum. This was redissolved in IMS (1000 ml) and the solution was concentrated under reduced pressure to a gum. The dilution and re-concentration were repeated twice more, and the final gum was redissolved in IMS (350 ml).

Meanwhile, a mixture of triethylorthoformate (900 ml) and tetrahydrofuran (THF) (400 ml) was prepared and cooled to 0 to 5° C. Concentrated hydrochloric acid (80 ml) was added, maintaininglthe temperature between 0 and 10° C., and more THF (100 ml,) was then added. To this mixture was added the IMS concentrate prepared above, which was rinsed in with IMS (100 ml). The mixture was warmed to 20 to 25° C. and seeded with authentic (1S,4R)-c-4-[2-amino-6-chloro-9H-purin-9-yl]-2-cyclopentene-1-methanol hydrochloride salt and stirring continued for about 20 h. The slurry was filtered, the solid was washed with a mixture of tert-butyl methyl ether and IMS (9/1, 3×300 ml) and dried in vacuo at 40 to 45° C. to give the title compound (117 g, 82%) as a fawn coloured solid $^1$H-NMR (DMSO-d$_6$)δ: 8.38(s, 1, purine CH), 7.50(br m, ca 5, NH$_3^+$, OH, HOD), 6.20(m, 1, =CH) 5.94(m, 1, =CH), 5.49(m, 1, NCH), 3.46(m, 2, OCH$_2$), 2.91(br m, 1, CH), 2.70-2.60(m, 1, CH), 1.75-1.66(m, 1, CH).

Example B
Preparation of (1S,4R)-cis-4-[2-amino-6-chloro-9H-purin-9-yl]-2-cyclopentene-1-methanol hydrochloride salt.

A suspension of (1R,4S)-cis-[4-(hydroxymethyl)-2-cyclopentene-1-yl]carbamic acid, 1, 1-dimethylethyl ester (100 g) in industrial methylated spirit (IMS) (600 ml) was treated with concentrated hydrochloric acid (48 ml, 1.2 molar equivalents) and the resultant solution was heated to the boil over about 0.5 h. Heating under reflux was maintained for about 3 h. The solution was cooled to 20 to 25° C. and sodium bicarbonate (103.4 g) was added followed by N-(2-amino-4,6-dichloro-5-pyrimidinyl)formamide (WO95/21161) (97g) and IMS (600 ml). The suspension was heated under reflux for about 4 h and then cooled to about −5° C. After stirring at this temperature for about 1h, the solids were filtered off and washed with IMS (2×100 ml). The combined filtrates and washings were concentrated under reduced pressure to a residual volume of about 400 ml. This was redissolved in IMS (1000 ml) and the solution was concentrated under reduced pressure to a gum. The dilution and re-concentration were repeated twice more, and the final gum was redissolved in IMS (350 ml).

Meanwhile, triethylorthoformate (900 ml) was cooled to 0 to 5° C. and concentrated hydrochloric acid (80 ml) was added, maintaining the temperature between 0 and 10° C. To this mixture was added the IMS concentrate prepared above, which was rinsed in with IMS (600 ml). The mixture was warmed to 20 to 25° C. and seeded with authentic (1S,4R)-cis-4-[2-amino-6-chloro-9H-purin-9-yl]-2-cyclopentene-1-methanol hydrochloride salt and stirring was continued for about 7 h. The slurry was filtered, and the solid was washed with IMS (2×150 ml) and dried in vacuo at 40 to 45° C. to give the title compound (114 g, 81%) as a fawn coloured solid, spectroscopically identical to the product of Example A.

Example C
Preparation of (1S,4R)-cis-4-[2-amino-6-chloro-9H-purin-9-yl]-2-cyclopentene-1-methanol hydrochloride salt.

A suspension of (1R,i4S)-cis-[4-(hydroxymethyl)-2-cyclopentene-1-yl]carbamic acid, 1, 1-dimethylethyl ester (72.5 kg) in industrial methylated spirit (IMS) (435 L) and water (about 200 L) was treated with concentrated hydrochloric acid (36.5 L, 1.2 molar equivalents) and the resultant solution was heated to the boil over about 1.5 h. Heating under reflux was maintained for about 2 h. The solution was cooled to 20 to 25° C. and sodium bicarbonate (75 kg) was added followed by N-(2-amino-4,6-dichloro-5-pyrimidinyl) formamide (WO95/21161) (70 kg) and IMS (435 L). The suspension was heated under reflux for about 4 h and then cooled to about −5° C. After stirring at this temperature for about 1 h, the solids were filtered off and washed with IMS (2×144 L). The combined filtrates and washings were concentrated under reduced pressure to a residual volume of about 290 L. This was diluted with IMS (about 300 L) and the solution was concentrated under reduced pressure to a residual volume of about 290 L. The dilution and re-concentration were repeated twice more, and the final concentrate was diluted with IMS (610 L) and heated to about 35–40° C. The resultant mixture was filtered and the solids were washed with IMS (2×144 L) The combined filtrate's and washings were concentrated under reduced pressure to a residual volume of about 290 L and then diluted with IMS (217 L).

Meanwhile, a mixture of triethylorthoformate (660 L), concentrated hydrochloric acid (58 L) and IMS (72 L) was prepared at 0 to 8° C., To this mixture was added the IMS concentrate prepared above, which was rinsed in with IMS (2×72 L). The mixture was warmed to 20 to 25° C. and seeded with authentic (1S,4R)-cis-4-[2-amino-6-chloro-9H-purin-9-yl]-2-cyclopentene-1-methanol hydrochloride salt and stirring was continued for about 7 h. The slurry was cooled to 18–21° C., filtered, and the solid was washed with IMS (72 L and 217 L) and dried in vacuo at 40 to 45° C. to give the title compound (81.7 kg, 79.5%) as a fawn coloured solid, spectroscopically identical to the product of Example A.

Example D
Preparation of (1S,4R)-cis-4-[2-amino-6-chloro-9H-purin-9-yl]-2-cyclopentene-1-methanol hydrochloride salt.

A suspension of (1R,14S)-cis-[4-(hydroxymethyl)-2-cyclopentene-1-yl]carbamic acid, 1, 1-dimethylethyl ester (10 g) in industrial methylated spirit (IMS) (60 ml) was treated with concentrated hydrochloric acid (5 ml, 1.2 molar equivalents) and the resultant solution was heated to the boil over about 0.5 h. Heating under reflux was maintained for about 3 h. The solution was cooled to 20 to 25° C. and weighed (45.7 g). A portion (14 g) was diluted with IMS (14 ml) and sodium bicarbonate (3.1 g) was added followed by 2,5-diamino-4,6-dichloropyrimidine (WO95/21161) (2.0 g). The suspension was heated under reflux for about 7 h and then cooled to about −5° C. The solids were filtered off and the combined filtrates and washings were concentrated under reduced pressure to a gum, which was redissolved in IMS (17 ml).

Meanwhile, triethylorthoformate (21.4 ml) was cooled to 0 to 5° C. and concentrated hydrochloric acid (1.9 ml) was added, maintaining the temperature between 0 and 10° C. To this mixture was added the IMS solution prepared above, which was rinsed in with IMS (2×2.5 ml). The mixture was warmed to 20 to 25° C. and seeded with authentic (1S,4R)-cis-4-[2-amino-6-chloro-9H-purin-9-yl]-2-cyclopentene-1-methanol hydrochloride salt and stirring was continued for about 19 h. The slurry was filtered, and the solid was washed with IMS (2×4.5 ml) and dried in vacuo at 40 to 45° C. to give the title compound (2.06 g, 61%) as a pale yellow solid, spectroscopically identical to the product of Example A.

What is claimed is:

1. A process for the preparation of a compound of formula (1),

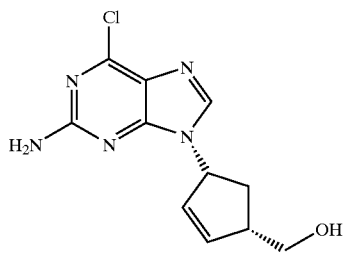
(I)

optionally in the form of its salt complex comprising, hydrolyzing a compound of formula (IV)

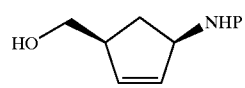
(IV)

wherein P is a protecting group, in the presence of an acid, condensing the product of formula (V)

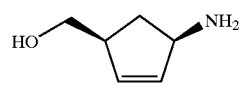
(V)

formed in situ in the presence of a base with a compound of formula (VI)

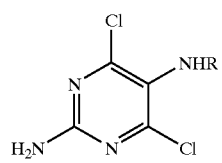
(VI)

in which R represents CHO or H, followed by ring closure in situ of the resulting intermediate of formula (VII)

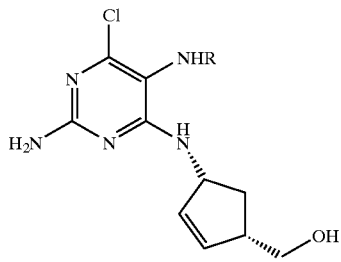
(VII)

in which R represents CHO or H, with a trialkylorthofornate, in the presence of a mineral acid, to produce a compound of formula (1), which can then be optionally reacted with an acid to form its salt.

2. A process as claimed in claim 1 wherein R is CHO.

3. A process as claimed in claim 1 wherein P is an acyl or substituted oxycorbonyl group.

4. A process as claimed in claim 3 wherein P is a formyl, $C_{1-4}$ alkanoyl group, or an oxycarbonyl group of formula R'OC(O) wherein R' is alkyl or aralkyl.

5. A process as claimed in claim 4 wherein P is an acetyl group or R' is tert butyl or benzyl.

6. A process as claimed in claim 1 wherein the hydrolysis step is carried out in an alkanol, a cylic ether, or a chlorinated hydrocarbon in the presence of an organic or mineral acid.

7. A process as claimed in claim 6 wherein the hydrolysis step is carried out in IMS and the acid is trifluorloacetic acid or hydrochloric acid.

8. A process as claimed in claim 1 wherein the condensation reaction is carried out under reflux in a polar solvent in the presence of base.

9. A process as claimed in claim 8 wherein the polar solvent is an alcohol, water, or acetonitrile and the base is trialkylamine or an alkali metal carbonate or bicarbonate.

10. A process as claimed in claim 9 wherein the base is potassium or sodium carbonate or sodium bicarbonate.

11. A process as claimed in claim 1 wherein the trialkylorthoformate is triethylorthoformate and the mineral acid is sulfuric acid.

12. A process as claimed in claim 1 wherein the ring closure reaction is carried out using triethylorthoformate in the presence of hydrochloric acid.

13. A process as claimed in claim 1 wherein the reacting in situ of the intermediate of formula (VII) with a trialkylorthoformate, in the presence of a mineral acid, is conducted in the presence of one or more non-aqueous solvents selected from tetrahydrofuran, ethyl acetate, or IMS.

* * * * *